United States Patent [19]

Lemieux et al.

[11] 4,238,473

[45] Dec. 9, 1980

[54] ARTIFICIAL OLIGOSACCHARIDE ANTIGENIC DETERMINANTS

[75] Inventors: Raymond U. Lemieux, Edmonton; David R. Bundle, Ottawa; Donald A. Baker, Edmonton, all of Canada

[73] Assignee: Chembiomed Limited, Edmonton, Canada

[21] Appl. No.: 5,579

[22] Filed: Jan. 22, 1979

Related U.S. Application Data

[63] Continuation-in-part of Ser. No. 698,548, Jun. 21, 1976, Pat. No. 4,137,401.

[30] Foreign Application Priority Data

Jul. 8, 1975 [GB] United Kingdom ............... 28729/75

[51] Int. Cl.$^3$ ...................... A61K 35/14; C07H 13/06
[52] U.S. Cl. ........................................ 424/11; 424/85; 424/180; 536/1; 536/4; 536/18; 536/53; 536/115; 536/116; 536/119; 536/120
[58] Field of Search ...................... 536/4, 1, 120, 116, 536/18, 53; 424/180, 11, 85

[56] References Cited

U.S. PATENT DOCUMENTS

| | | | |
|---|---|---|---|
| 3,356,674 | 12/1967 | Ikeda et al. ............................. | 536/4 |
| 3,655,645 | 4/1972 | Jacques ................................. | 536/116 |
| 3,729,461 | 4/1973 | Pomeranz et al. ..................... | 536/4 |
| 4,137,401 | 1/1979 | Lemieux et al. ...................... | 536/116 |

*Primary Examiner*—Johnnie R. Brown
*Attorney, Agent, or Firm*—Alan A. Thomson

[57] ABSTRACT

Carbohydrate antigenic determinants containing a glycosidically linked bridging arm are synthesized and coupled to carrier molecules to form artificial antigens, and to solid supports to form immunoadsorbents. Various artificial antigens of the blood group type are prepared and applications shown. Specific examples are given to the synthesis of the Lewis-a, Lewis-b, A, B, and H(O) blood group antigens; to the preparation of antisera to these artificial antigens, to the preparation of immunoadsorbents specific for antibodies to these antigens, and to the detection of such antigens wherever they occur.

26 Claims, No Drawings

ARTIFICIAL OLIGOSACCHARIDE ANTIGENIC DETERMINANTS

This application is a continuation-in-part of application Ser. No. 698,548 filed June 21, 1976 (which issued to U.S. Pat. No. 4,137,401 on Jan. 30, 1979.

In the parent application, a general methodology for the preparation of oligosaccharide antigenic determinants in a form suitable for the preparation of artificial antigens and immunoadsorbents was disclosed. In this continuation-in-part, we will describe and claim some applications of the parent-disclosed technology in the particular area of carbohydrate blood group antigens.

Because it is the simplest tissue to study, a large number of human antigens were first identified on the red cell. Many of these antigens have carbohydrate determinants, notably the A, B, H(O) antigens, and are referred to as blood group antigens despite the fact that they are now known not to be confined to the red cell but are widely distributed throughout the body in tissue and secretions.

As will be seen from the further examples given below (XX–XXV), through the methodologies disclosed in this invention, it is now possible to detect these blood group antigens having carbohydrate determinants wherever they occur on tissues or in secretions.

SUMMARY OF THE INVENTION

It is the objective of the present invention to provide processes to chemically synthesize carbohydrate antigenic determinants in a form suitable for linkage to carrier molecules or solid supports. The invention further concerns the use of the products of the process for the following purposes:

(a) preparation of artificial carbohydrate antigens.
(b) preparation of antisera specific for the carbohydrate hapten of the artificial antigen.
(c) preparation of immunoadsorbents (affinity adsorbents) capable of selectively adsorbing antibodies raised to either the artificial antigen or to natural antigens possessing the same terminal oligosaccharide structure as the antigenic determinant.
(d) detection of blood group antigens having carbohydrate determinants.

Particular reference is made to the lower oligosaccharide antigenic determinants of the human blood groups, e.g. Lewis-a, Lewis-b, A, B and H(O) (Type I).

The novel products of the invention are lower oligosaccharide compounds comprising chosen aldoses O-α- or O-β-glycosidically linked to form di-, tri-, or tetrasaccharides, and having a bridging arm O-β-glycosidically linked to one of the aldose moieties, the bridging arm having the structure:

O—R—COR"

where R is an aliphatic hydrocarbon moiety having from 3 to 17 carbon atoms and R" is —H, —OH, —NH₂, —NHNH₂, —N₃ or lower alkoxy; the aldoses and their linkage configurations being chosen to give active blood group determinants. Specific di-, tri-, and tetra-saccharide blood group determinants are described in the Examples.

The present invention includes a process for preparing oligosaccharide plus bridging arm compounds active as blood group determinants comprising:

(1) reacting (a) an activated aldose selected from an aldose halide, a 1,2-orthoacyl ester-aldose derivative, or a 1,2-oxazoline-aldose derivative, with
  (b) a monohydroxy carboxylic acid of the general structure HO—R—COOR' where R is an aliphatic hydrocarbon moiety having from 3 to 17 carbon atoms and R' is a protecting alkyl group, to form an O-β-glycoside of the structure

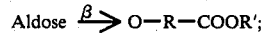

(2) linking O-glycosidically in either the α- or β-anomeric configuration a further aldose to the initial aldose moiety to form a disaccharide; and choosing the aldoses and their linkage configurations to give active blood group determinants.

This latter process may be further expanded with additional steps for the preparation of trisaccharides and tetrasaccharides of structure respectively,

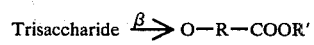

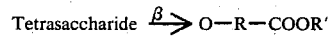

and recovering said compounds as novel haptens.

In addition there is provided a process for the preparation of artificial antigens and immunoadsorbents by attaching the monosaccharide or lower oligosaccharide, plus bridging arm compound to a soluble carrier macromolecule or to an insoluble support.

DETAILED DESCRIPTION

A detailed description of the present invention will now be given. Special reference will be made to the synthesis of the antigenic determinants for the human blood groups Lewis-a, Lewis-b, B and H(O) as examples, but the same techniques apply to other carbohydrate antigens. The overall process begins with the attachment of an appropriately selected sugar (for example, 2-acetamido-2-deoxy-D-glucose (D-glcNAc) for the Lewis-a, -b and H(O) determinants and D-galactose (D-gal) for the B determinant) by way of a β-glycosidic linkage to a protected monohydroxycarboxylic acid of structure I.

HO—R—COOR'    I

The attachment is accomplished following procedures for the synthesis of β-glycosides in principle known in carbohydrate chemistry and may follow β-glycosidation procedures such as the Koenigs-Knorr-Helferich-type methods using O-acetylated α-glycosyl halide derivatives of the sugar[7–10] or in the case of D-galactose by way of an O-acylated-1,2-orthoacyl ester derivative[11] and in the case of D-glucosamine by way of an O-acylated 1,2-oxazoline derivative[12] and, in each of the latter cases, the use of a suitable acid catalyst for promotion of the reaction. In this way the first products (structure II) are prepared.

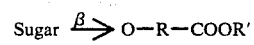

The aglycon (—O—R—COOR') of structure II is selected under the following conditions. The group R' is selected from the lower alkyl groups such as methyl, ethyl, n-propyl, isopropyl, and n-butyl with some preference given to the methyl group for reasons of economy and generally more convenient reactivity of the methoxycarbonyl group over other alkoxycarbonyl groups. The —R— group provides a physical separation, a bridging arm, between the antigenic determinant and the carrier or support. This group should be inert towards the chemical reactions used for the further elaboration of the carbohydrate structure and is thereby effectively limited to structures that are hydrocarbon or equivalent in composition. The preferred structures correspond to that shown below, where n is in the range 3 to 17.

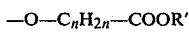

and the carbon chain is normal. Particularly useful are structures where the value of n is in the range 8–10 not only in view of the ready availability of the parent hydroxy-acid but also because the inert rather featureless aliphatic chain appears to function as an internal adjuvant. Thus, higher antibody titres are obtained using bridging arms of this length as opposed to those of shorter length. Most examples in this invention utilize —R— equal to —$C_8H_{16}$— since with this grouping very high titer antisera were consistently achieved.

The β-glycoside derivative products will have the structure

where R is an aliphatic hydrocarbon moiety having 3 to 17 carbon atoms and R″ is —H, —OH, —$NH_2$, —$NHNH_2$, —$N_3$, or lower alkoxy, and n has a value of 1 to 4. Thus the

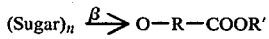

where R′ is a protecting group, may be converted to the product

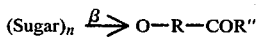

where the R″ may constitute other than a protecting group. The initial protecting group —OR′, e.g. the methyl, ethyl, propyl and butyl esters, may be replaced with other R″ groups either to form alternative haptens for a particular application or to facilitate coupling to a carrier or support.

The following four specific preparations exemplify the preparation of compounds of structure II. In all cases, the structures achieved were substantiated by modern methods of chemical analysis including carbon-13 and proton nuclear magnetic resonance spectra (cmr and pmr, respectively), elemental analysis and in many instances by high-resolution mass spectrometry.

EXAMPLE I

The antigenic determinant 8-methoxycarbonyloctyl β-D-galactopyranoside (1)

8-Methoxycarbonyl-1-octanol (21.4 g, 0.115 mole) and dried mercuric cyanide (30.3 g, 0.119 mole) were dissolved in a 1:1 mixture of dry distilled benzene-nitromethane (850 ml). The solution was stirred and 200 ml of solvent was distilled. Mixed solvent (200 ml) was added and calcium sulfate (40 g) was added followed by 2,3,4,6-tetra-O-acetyl-α-D-galactosyl bromide (38.7 g, 0.094 mole). The mixture was stirred at room temperature for 36 h and then heated at 70° for 2 h. After cooling, the solution was filtered and the filtrate evaporated in vacuo to give a yellow syrup. This syrup was dissolved in distilled ethyl acetate (500 ml) and the solution was washed with an aqueous solution (10% w/w, 500 ml) of sodium iodide. The organic phase was then washed successively with a saturated solution of sodium thiosulphate (200 ml) and $H_2O$ (2×250 ml). The organic phase was dried over sodium sulphate and then evaporated in vacuo after filtration. This syrup (~50 g) after drying under high vacuum overnight was dissolved in dry distilled methanol (200 ml) and to this solution, 200 ml of methanolic sodium methoxide (150 mg of sodium) was added. After stirring at room temperature for 24 h, acid resin (prewashed a few times in methanol) was added and stirred until the pH was neutral. After filtration, the solution was evaporated and the waxy residue dissolved at room temperature in 100 ml of $H_2O$. This solution was extracted with ether (2×40 ml) and then placed in the fridge. Upon standing, crystallization occurred. The white crystals were filtered and dried. Weight 13.5 g (41%), mp 104°–105°, $[\alpha]_D^{25}$ −13.4° (c 1, 95% ethanol).

EXAMPLE II

The antigenic determinant 8-ethoxycarbonyloctyl 2-acetamido-2-deoxy-β-D-glucopyranoside (2)

Mercuric cyanide (31.8 g, 126 mmol) and anhydrous calcium sulfate were added to a solution of 8-ethoxycarbonyl-1-octanol (25 g, 124 mmol) in 100 ml of dry benzene. The mixture was protected from moisture while stirring for 1 h at room temperature prior to addition of 2-acetamido-3,4,6-tri-O-acetyl-2-deoxy-α-D-glucopyranosyl chloride (25 g, 68 mmol). The mixture was efficiently stirred for 4 days at room temperature. Dichloromethane (400 ml) was added, the solids were removed by filtration, and the filtrate was sequentially washed with 10% aqueous sodium chloride solution (50 ml), once with saturated aqueous sodium bicarbonate solution (25 ml), and twice with water (50 ml). In each case, the aqueous layer was back-extracted with a little dichloromethane. After drying over magnesium sulfate, the solvents were removed to leave a syrup which crystallized from a mixture of diethyl ether and n-hexane. The crude yield of 8-ethoxycarbonyloctyl 2-acetamido-3,4,6-tri-O-acetyl-2-deoxy-β-D-glucopyranoside was 28.9 g (80%). A recrystallized sample showed mp 112°, $[\alpha]_D^{20}$ −12.2° (c 2.4, chloroform). De-O-acetylation of this compound with triethylamine (27 ml) in methanol (500 ml) at 0°–5° for 18 h gave after evaporation of the solvent compound 2 as a chromatographically homogeneous powder which resisted crystallization and was therefore characterized as its hydrazide derivative mp 200°–201°, $[\alpha]_D^{26}$ −22.5° (c 1, water), prepared by treating 2 with an 85% solution of hydrazine hydrate.

An alternate preparation of the antigenic determinant 2

A mixture of p-toluene sulfonic acid (10 mg), 8-ethoxycarbonyl-1-octanol (1 g), 2-methyl-4,5-(3,4,6-triacetyl-2-deoxy-α-D-glucopyrano)-Δ²-oxazoline (1 g) was dissolved in 10 ml of a 1:1 mixture of benzene and nitromethane and refluxed for 3 hours. The usual workup gave 8-ethoxycarbonyl-octyl 2-acetamido-3,4,6-tri-O-acetyl-2-deoxy-β-D-glucopyranoside (1.28 g, 79%).

De-O-acetylation as described in example II gave the title antigenic determinant in 90% yield.

EXAMPLE III

The antigenic determinant 8-methoxycarbonyloctyl 2-acetamido-2-deoxy-β-D-glucopyranoside (3)

Compound 3 was prepared as described in example VI below.

EXAMPLE IV

The antigenic determinant 5-methoxycarbonylpentyl 2-acetamido-2-deoxy-β-D-glucopyranoside (4)

Condensation of 2-acetamido-3,4,6-tri-O-acetyl-2-deoxy-α-D-glucopyranosyl chloride with 5-ethoxycarbonyl-1-pentanol under the same conditions as reported in example II gave a 74% yield of 5-ethoxycarbonylpentyl 2-acetamido-3,4,6-tri-O-acetyl-2-deoxy-β-D-glucopyranoside, mp 101°–102°, $[\alpha]_D^{25}$ −16.8° (c 1.06, chloroform). De-O-acetylation of this compound using sodium methoxide gave after crystallization a 92% yield of 4 mp 154°–155° (melts and resolidifies) remelts 167°, $[\alpha]_D^{18}$ −25.5° (c 1.1, water).

This invention utilizes compounds of general structure II for the elaboration of more complex antigenic determinants. In such processes, additional sugars are added to appropriately blocked derivatives of II using synthetic methodologies in principle known to carbohydrate chemistry. In this fashion, structures of type III are achieved wherein a disaccharide unit is present in contrast to the simple monosaccharide units in II.

  III

Examples V, VI, and VII illustrate the preparation of compounds of general structure III.

EXAMPLE V

The antigenic determinant 8-methoxycarbonyloctyl 2-O-(α-L-fucopyranosyl)-β-D-galactopyranoside (5)

To a colorless solution of 6.6 g of α,α-dimethoxytoluene (0.043 mole) in 60 ml of distilled acetonitrile, p-toluenesulfonic acid (0.285 g, recrystallized) was added. The solution instantaneously became yellow and immediately 8-methoxycarbonyloctyl β-D-galactopyranoside (10 g, 0.028 mole) was added. The yellow color disappeared within 5 minutes and dissolution took place in 30 minutes. The solution, protected from humidity, was stirred at room temperature for 44 hours. At this time, no starting material was detectable by thin layer chromatography (tlc) and a new product 8-methoxycarbonyloctyl 4,6-O-benzylidene-β-D-galactopyranoside was present. The presence of the isomeric 3,4-O-benzylidene analog of this compound could not be detected by tlc. A few drops of triethylamine were added (pH ~7) and the solvent was evaporated. Toluene was added to the residual syrup and then evaporated in vacuo and this operation was repeated once more. The white waxy solid was then stirred overnight with hexane (distilled) to remove a fast running uv absorbing spot, and a very fine powder was obtained. After filtration, the solid was dissolved in dichloromethane (distilled, 500 ml) and the solution washed with a saturated sodium bicarbonate solution (100 ml) and then water (300 ml). After drying over sodium sulfate, the organic phase was evaporated to dryness to give the pure 4,6-benzylidene derivative. The product in solution in methanol was placed in a dessicator containing n-pentane for crystallization. The yield of recrystallized product was 83%, mp 127°–128°, $[\alpha]_D^{25}$ −33° (c 1, chloroform). A portion of the benzylidinated compound (7 g, 0.016 mole) was dissolved in 400 ml of dry distilled dichloromethane containing 10 ml of pyridine (distilled). The solution was cooled to −40° and 2 ml (0.017 mole) of distilled benzoyl chloride was added dropwise. After 2 h at that temperature tlc examination showed the presence of only one product, 8-methoxycarbonyloctyl 3-O-benzoyl-4,6-O-benzylidene-β-D-galactopyranoside. Ice chips were added and the solution was poured in a mixture of water and ice (300 ml) vigorously stirred. The organic phase was separated and the aqueous phase back-extracted with dichloromethane (2×100 ml). The combined organic phase was washed with a saturated sodium bicarbonate solution (200 ml) and then with water (2×300 ml). After drying over sodium sulphate, the organic phase was evaporated to dryness. The remaining pyridine was co-evaporated with toluene in vacuo to give 8.7 g (100%) of the desired blocked galactopyranoside. Recrystallization was achieved by dissolving the syrup in 2-propanol and the solution was placed in a desiccator containing n-pentane. The yield was quantitative, mp 96°–97°, $[\alpha]_D^{25}$ +60.5° (c 1, chloroform).

The above selectively blocked galactopyranoside (4 g, 7.38 mmol) was dissolved in a mixture of purified dichloromethane (10 ml) and distilled N,N-dimethylformamide (0.62 ml) containing 1.6 g (10.7 mmol) of tetraethylammonium bromide and 7.8 g of diisopropylethylamine. To the solution tri-O-benzyl-α-L-fucosyl bromide (freshly prepared from 20.8 mmol of tri-O-benzyl-1-p-nitrobenzoyl-α-L-fucopyranose) was added, followed by addition of 2 g of molecular sieves 4 Å. After 48 h ml) and the solids were removed by filtration. The filtrate was washed with water and dried over sodium sulphate. After filtration, the solution was evaporated in vacuo to a pale yellow syrup. This syrup was dissolved in ether-ethyl acetate (3:2) and applied to an alumina column. The products were rapidly eluted with the same solvent system and obtained as a pale yellow syrup upon evaporation of the solvents. This syrup was dissolved in hexane-ethyl acetate (8:2) and applied to a silica gel (200 g) column. The elution was performed using the same solvent mixture. Two fast running spots were eluted first, then the desired compound. The weight (after being dried under high vacuum) was 6.1 g (86%).

De-O-benzoylation with methanolic sodium methoxide gave 8-methoxycarbonyloctyl 4,6-O-benzylidene-2-O-(tri-O-benzyl-α-L-fucopyranosyl)-β-D-galactopyranoside in 80% yield, mp 104°–105°, $[\alpha]_D^{25}$ −54° (c 1, chloroform). Hydrogenation over 5% palladium on charcoal gave the title compound 5 as a tlc homogeneous syrup which was characterized as its hydrazide derivative, mp 178° (ethanol-ether), $[\alpha]_D^{18}$ −87.4 (c 1.02, water).

EXAMPLE VI

The antigenic determinant 8-methoxycarbonyloctyl 2-acetamido-2-deoxy-4-O-(α-L-fucopyranosyl)-β-D-glucopyranoside (6)

Sodium (18 mg) was added to dry methanol (40 ml) and after the reaction was complete 8-ethoxycarbonyloctyl 2-acetamido-3,4,6-tri-O-acetyl-2-deoxy-β-D-glucopyranoside (1.06 g, 2 mmol) was added. The solution was kept at room temperature for 24 h prior to deionization using the acid resin. Solvent removal left 753 mg of the de-O-acetylated product which was not characterized but used directly for the preparation of the title compound. The material, dried in vacuo over phosphorus pentoxide, was dissolved in DMF (5 ml) which contained α,α-dimethoxytoluene (2 ml) and p-toluenesulfonic acid (25 mg). After heating at 40° for 1.5 h, the solution was cooled and triethylamine added to neutralize the acid. After solvent removal, toluene (5 ml) was added and removed by evaporation. This procedure was repeated twice and the residue then triturated with hexane (10 ml). The solid was collected and dissolved in dichloromethane (25 ml). The solution was washed three times with water (5 ml), dried over magnesium sulfate, and evaporated to a residue which crystallized from ethanol-petroleum ether. The yield of 8-methoxycarbonyloctyl 2-acetamido-4,6-O-benzylidene-2-deoxy-β-D-glucopyranoside was 481 mg (50%), mp 219°. Recrystallization gave the analytical sample, mp 221°, $[\alpha]_D^{25} -56°$ (c 1.3, dimethylformamide).

This compound was acetylated using a 1:1 mixture of acetic anhydride and pyridine for 24 h. The product was isolated in the usual manner and de-O-benzylidinated using 50% acetic acid at 100° for 25 min to yield 2-acetamido-3-O-acetyl-2-deoxy-β-D-glucopyranoside, mp 122°-123°, $[\alpha]_D^{30} -47.3$ (c 1.1, chloroform).

The 6-position of this compound was selectively benzoylated in 88% yield by treatment with 1.1 equivalents N-benzoylimidazole. A mixture of the above 6 benzoate, 8-methoxycarbonyloctyl 2-acetamido-3-O-acetyl-6-O-benzoyl-2 2-deoxy-β-D-glucopyranoside, mp 105°, $[\alpha]_D^{32} -42.0°$ (c 1, chloroform), (1.55 g, 2.9 mmol) tetraethylammonium bromide (630 mg, 3 mmol), diisopropylethylamine (450 mg) and DMF (4 ml) in dichloromethane 20 ml was added to 2,3,4-tri-O-benzyl-α-L-fucopyranosyl bromide freshly prepared from 3.38 g, 5.8 mmol, of 2,3,4-tri-O-benzyl-1-O-p-nitrobenzoyl-β-L-fucopyranose. The solution was stirred at room temperature for three days after which time tlc examination no longer showed the presence of any starting material. Dichloromethane (150 ml) was added and the solution was washed in the usual manner with water and aqueous sodium bicarbonate solution prior to solvent removal.

The syrupy product was used directly for the preparation of 8-methoxycarbonyloctyl 2-acetamido-4-O-(2,3,4-tri-O-benzyl-α-L-fucopyranosyl)-2-deoxy-β-D-glucopyranoside. The crude disaccharide (3.78 g) was dissolved in 50 ml of dry methanol, and 5 ml of 0.2 N sodium methoxide in methanol was added. After 24 h at room temperature, the solution was deionized using the acid resin. Solvent removal left an oil which was dissolved in dichloromethane (100 ml). The solution was washed with water and dried over magnesium sulfate prior to evaporation to a residue (1.01 g, 85% yield) from the fully blocked disaccharide. Purification was by recrystallization from ethyl acetate-hexane, mp 145°-146°, $[\alpha]_D^{25} -33.6°$ (c 1.2, chloroform).

Hydrogenation of this compound in ethanol over 5% palladium on charcoal at 50 psi and 70° for 3 days gave after removal of the solvent and catalyst compound 6 as an amorphous solid, $[\alpha]_D^{25} -95.5°$ (c 1.0, water) in 97% yield.

EXAMPLE VII

The antigenic determinant 8-Ethoxycarbonyloctyl 2-acetamido-2-deoxy-3-O-(β-D-galactopyranosyl)-β-D-glucopyranoside (7)

Compound 2 (6.3 g, 15.5 mmol) was added to a stirred solution of anhydrous zinc chloride (7.0 g) in freshly distilled benzaldehyde (100 ml) to which was added an anhydrous calcium sulfate (14 g). After 20 h at room temperature, the solids were removed by filtration. The addition of hexane (500 ml) to the filtrate caused the precipitation of a gummy precipitate which was triturated several times with hexane. The residue was then triturated with pyridine (7 ml) prior to the addition of dichloromethane (300 ml). The resulting solution was washed twice with water (25 ml), twice with saturated aqueous sodium bicarbonate solution (25 ml), and twice again with water (25 ml). Solvent removal, after drying over sodium sulfate, left a residue which crystallized from ethanol (4.68 g, 61% yield), mp 210°-220°. The melting point was unchanged by recrystallization from aqueous methanol, $[\alpha]_D^{24} -55.5°$ (c 1.3, chloroform).

A solution of this compound (12.1 g, 24.5 mmol) and mercuric cyanide (7.35 g, 30 mmol) in 1600 ml of a 1:1 mixture of benzene and nitromethane was distilled at atmospheric pressure to remove 100 ml of solvent. Calcium sulfate (40 g) and tetra-O-acetyl-α-D-galactopyranosyl bromide (12.3 g, 29.6 mmol) were added, after cooling, and the temperature was then maintained at 50° for 20 hours. Tetra-O-acetyl-galactosyl bromide (10 g, 24.4 mmol), mercuric cyanide (6.15 g), and calcium sulfate (10 g) were then added, and the mixture was stirred a further 20 h at 50°. TLC examination indicated the absence of the monosaccharide alcohol. The solids were removed by filtration and washed with dichloromethane (800 ml). The combined filtrates were twice washed with 30% aqueous potassium iodide solution (50 ml), twice with saturated aqueous sodium bicarbonate solution (50 ml), and then twice with water (50 ml). After drying over sodium sulfate, the solvent was removed to leave a syrup. The syrup was dissolved in a little hot ethanol and diethyl ether then added to near turbidity. The addition of petroleum ether caused the precipitation of a solid which was crystallized from ethyl acetate-hexane (17.1 g, 85%, mp 108°-109°). Recrystallization from ethyl acetate-diethyl ether afforded pure material, mp 110°-111°, $[\alpha]_D^{27} -8.2°$ (c 1.4, chloroform). Removal of the hydroxyl protecting groups in the manner described in previous examples gave 7 in 82% yield as a white solid, mp 207°-208°. Recrystallization from methanol raised the melting point to 211°-212°, $[\alpha]_D^{17} -22°$ (c 1, water).

Appropriately blocked derivatives of compounds of structure-type III and encountered in the preparations of compounds 5, 6 and 7 are used to elaborate by way of chemical synthesis structures of type IV,

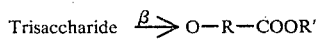

IV

Thus, the terminal trisaccharide IV units of important human blood group antigens are obtained. This is exemplified by the following preparations of the antigenic determinants for the Lewis-a, O(H) and B Human blood groups, in Examples VIII, IX and X respectively.

EXAMPLE VIII

The antigenic determinant 8-methoxycarbonyloctyl 2-acetamido-2-deoxy-4-O-(α-L-fucopyranosyl)-3-O-(β-D-galactopyranosyl)-β-D-glucopyranoside (8)

8-Ethoxycarbonyloctyl 2-acetamido-3-O-(tetra-O-acetyl-β-D-galactopyranosyl)-4,6-O-benzylidene-2-deoxy-β-D-glucopyranoside (7.65 g) (cf example VII) was de-O-benzylidinated using aqueous acetic acid under conditions similar to those used in example VI to give 5.6 g (81%) of product, mp 153.5°, $[\alpha]_D^{16}+9.6°$ (c 1.4, chloroform). A portion of this material (1.47 g, 2 mmol) w as selectively acetylated at the 6-position using N-acetyl imidazole (2.2 mmol) to yield 1.10 g (71%) of 8-ethoxycarbonyloctyl 2-acetamido-6-O-acetyl-3-O-(tetra-O-acetyl-β-D-galactopyranosyl)-2-deoxy-β-D-glucopyranoside, as a tlc homogeneous syrup, $[\alpha]_D^{31}+6.2°$ (c 1, chloroform).

A mixture of this compound (3.0 g, 3.86 mmol), tetraethylammonium bromide (840 mg, 4 mmol), diisopropylethylamine (600 mg, 4.64 mmol), dichloromethane (25 ml), and DMF (5 ml) was added to tri-O-benzyl-fucosyl bromide (2.56 g, 5.15 mmol) dissolved in dichloromethane (5 ml) and DMF (1 ml) was then added, and the solution was stirred for an additional 3 days. Dichloromethane (300 ml) was added, and the product was isolated in the usual manner. Purification was effected by chromatography on a silica gel column (75×3.5 cm). Development with 1:1 ethyl acetatehexane (300 ml) was followed by the same solvent but to which 5% ethanol was added. The first band to appear soon after changing solvent provided the blocked trisaccharide as a tlc homogeneous syrup (4.36 g, 94), $[\alpha]_D^{22}-54°$ (c1.1, chloroform). Removal of the hydroxyl protecting groups by methods similar to those already described gave the desired antigenic determinant 8 as an amorphous solid, $[\alpha]_D^{25}-73.5°$ (c 1, water).

EXAMPLE IX

The antigenic determinant 8-methoxycarbonyloctyl 2-acetamido-2-deoxy-3-O-(2-O-[α-L-fucopyranosyl]-β-D-galactopyranosyl)-β-D-glucopyranoside (9)

A solution of 8-methoxycarbonyloctyl 2-acetamido-4,6-O-benzylidene-2-deoxy-β-D-glucopyranoside (480 mg, 1 mmol) (cf example VI) and mercuric cyanide (304 mg, 1.2 mmol) in 50 ml of a 1:1 mixture of benzene and nitromethane was distilled at atmospheric pressure to remove 10 ml of solvent. Powdered calcium sulfate (1.5 g) and the bromide (prepared from 900 mg of 3,4,6-tri-O-benzyl-1,2-di-O-p-nitrobenzoyl-β-D-galactopyranose) in 5 ml of a 1:1 benzene nitromethane mixture were added after cooling, and the temperature then maintained at 40° for 36 h. Tlc examination at this point indicated that no bromide remained. The reaction mixture was diluted with dichloromethane (25 ml), filtered and the filter cake washed with dichloromethane (3×10 ml). The combined filtrate and washings were made up to 200 ml with dichloromethane and washed with 30% aqueous potassium iodide (10 ml), saturated sodium bicarbonate solution (10 ml) and water (2×10 ml). After drying over sodium sulfate the solvent was removed leaving a syrup which was dissolved in a small amount of dichloromethane and applied to a column of silica gel D-O (65 g). The column was first developed with a mixture of benzene-ethyl acetate (4:1) and then the product was eluted with a 2:1 benzene-ethyl acetate mixture. Solvent removal afforded 550 mg (52%) of the blocked disaccharide which was crystallized from ethanol, mp 152°-153°, $[\alpha]_D^{24}+42.0°$ (c 1.1, chloroform).

This disaccharide (400 mg) was suspended in 40 ml anhydrous methanol containing 12 mg sodium and the reaction mixture stirred for 24 h at room temperature. The solution was de-ionized with acid resin and the residue obtained after evaporation of the solvent was dissolved in benzene and applied to a 4 g column of silica gel D-O. After washing the column with benzene to remove the methyl p-nitrobenzoate the product was eluted with benzene-ethyl acetate 2:1. Evaporation of the eluent afforded 260 mg (78%) of the de-O-p-nitrobenzoylated compound as a tlc homogeneous syrup.

To a mixture of this compound (1.03 g, 1.13 mmol), tetraethylammonium bromide (317 mg, 1.5 mmol), diisopropylethylamine (194 mg, 1.5 mmol) molecular sieves 4Å (1 g), dichloromethane (8 ml) and dimethylformamide (0.6 ml) was added 2,3,4-tri-O-benzyl-α-L-fucopyranosyl bromide freshly prepared from 2,3,4-tri-O-benzyl-1-O-p-nitrobenzoyl-β-L-fucopyranose (1.459 g, 2.5 mmol) in dichloromethane (2 ml). After 4 days tlc examination showed that no starting material remained, 200 μl of methanol were then added and after 2 h the reaction mixture was diluted with 25 ml dichloromethane and filtered. The filtrate was made up to 100 ml with dichloromethane and washed in the usual manner with water and aqueous saturated sodium bicarbonate prior to solvent removal. Chromatography of the crude product on silica gel D-O using ethyl-acetate-hexane 1:1 as eluent gave the fully blocked trisaccharide (1.116 g, 74% of theoretical) as a tlc (benzene-ethyl acetate 2:1) homogeneous syrup.

A solution of this compound (890 mg) dissolved in 9 ml of dichloromethane containing 1.0 ml of 90% trifluoroacetic acid was allowed to stand at room temperature for 10 minutes. The reaction mixture was diluted with toluene (10 ml) and water (0.5 ml) and the solvents evaporated. Chromatography of the crude product on silica gel gave after crystallization from ethyl acetatepentane 530 mg (64% of theoretical yield) of the de-O-benzylidinated trisaccharide, mp 125°-126°, $[\alpha]_D^{24}-37.4°$ (c 1.1, chloroform).

To a solution of this compound (452 mg) in ethanol (7 ml) was added 300 mg of 5% palladium on charcoal and the mixture shaken under a 100 psi atmosphere of hydrogen for 36 hr. The catalyst was removed by filtration and washed with three 10 ml portions of hot ethanol. The combined filtrate and washings were evaporated and the product was dissolved in a small amount of water and freeze dried. The crude product 9, (255 mg, quantitative yield) was homogeneous by tlc (isopropanol-ammonium hydroxide-water 7:1:2) and crystallized from a mixture of methanol and ether, mp 195°, $[\alpha]_D-60.3°$ (c, 1.1, water).

EXAMPLE X

The antigenic determinant 8-methoxycarbonyloctyl 2-O-(α-L-fucopyranosyl)-(3-O-α-D-galactopyranosyl)-β-D-galactopyrano-side(10)

8-Methoxycarbonyloctyl 3-O-benzoyl-4,6-O-benzylidene-2-O-(tri-O-benzyl-α-L-fucopyranosyl)-β-D-galactopyranoside (5 g, 5.2 mmol) (cf example V) in 250 ml of a freshly prepared methanolic sodium methoxide solution (1%) was stirred at room temperature for 2 h at which time the reaction was complete as judged by tlc. Sufficient acid ion exchange resin, prewashed with methanol, was added to neutralize the solution (pH≃7). The resin was removed by filtration and the filtrate evaporated in vacuo to give a pale yellow syrup (≃4.3 g). Crystallization from ethanol hexane gave 3.55 g (80%) of crystalline de-O-benzoylated compound, mp 104°–105°, $[\alpha]_D^{25} -54°$ (c 1, chloroform).

This compound (0.6 g, 0.7 mmol) was dissolved in dichloromethane (0.66 ml) and N,N-dimethylformamide (0.06 ml) containing tetraethylammonium bromide (0.16 g, 1 mmol), Hünigs base (0.27 g) and molecular sieve 4Å (1 g). Freshly prepared tetra-O-benzyl-α-D-galactopyranosyl bromide (1.04 g, 1.7 mmol) in a small amount of dichloromethane was then added and the reaction mixture was then stirred at room temperature for 48 hours. An additional portion (0.5 g, 0.85 mmol) of the bromo sugar was then added and the reaction mixture stirred for a further 24 hours. The reaction mixture was diluted with dichloromethane and the solids were removed by filtration. The filtrate was washed with water and dried over sodium sulphate. After filtration the solution was evaporated to a syrup. This syrup was purified by rapid chromatography on an alumina column before being applied to a silica gel column. Elution was obtained with ethyl acetate-hexane (2:8) and the desired blocked trisaccharide obtained pure by pooling the appropriate fraction. The yield was 0.686 g (71%), mp 82°–83° (recrystallized from heptane-ether).

To a solution of the above compound (600 mg, 0.43 mmol) in ethanol (10 ml) containing ethyl acetate (1 ml) was added 350 mg of 5% palladium on charcoal and the mixture was shaken under hydrogen at a pressure of 100 psi (gauge pressure) for 5 days. The catalyst was filtered off and washed with hot ethanol (3×5 ml). The combined filtrates were evaporated in vacuo to give compound 10 (177 mg, 62%). A portion was recrystallized from methanol-ether, mp 147°–150°.

Elaboration of appropriately blocked derivatives of structure type IV give tetrasaccharides of structure type V.

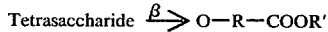   V

Thus, the terminal tetrasaccharide antigenic determinant of the human blood group Lewis-b is obtained as illustrated by Example XI.

EXAMPLE XI

The antigenic determinant 8-methoxycarbonyloctyl 2-acetamido-2-deoxy-4-O-(α-L-fucopyranosyl)-3-O-(2-O-[α-L-fucopyranosyl]-β-D-galactopyranosyl)-β-D-glucopyranoside (11)

8-Methoxycarbonyloctyl 2-acetamido-3-O-(3,4,6-tri-O-benzyl-2-O-[2,3,4-tri-O-benzyl-α-L-fucopyranosyl]-β-D-galactopyranosyl)-2-deoxy-β-D-glucopyranoside (620 mg, 0.5 mmol) (cf example IX) was selectively acetylated at the 6-position of the N-acetyl glucosamine residue by treatment with N-acetyl imidazole (0.6 mmol). α-Fucosylation of the compound as in example VIII gave the desired blocked tetrasaccharide in 70% yield as a tlc homogeneous syrup. Removal of the hydroxyl protecting groups by the methods previously described (cf example VIII) gave tetrasaccharide 11 in 80% yield.

The demonstration that synthesis can lead to large scale preparations of important active carbohydrate determinants means that mankind will no longer be dependent on rare and expensive sources of minute amounts of these determinants. The demonstration that active determinants can be produced in such a fashion and that these are readily employable for the preparation of effective highly immunogenic antigens promises to be of great utility for the provision of antibodies which are monospecific for the selected determinant. Thus, applications for the provision of typing sera for both blood sera and cells are indicated and demonstrated. Extension to the typing of tissues is evident and is expected to be of major utility for the proper matching of tissues for tissue transplantation operations. Antibodies raised against the wide range of carbohydrate determinants arising from the disclosure of this invention can serve as diagnostic reagents and in the preparation of affinity columns as now widely practiced using so-called lectins which are natural proteins possessing specific affinity for a carbohydrate structure. Of major importance is the provision of antisera specific to minor human blood groups such as Le$^a$ and Le$^b$. Effective typing sera for such minor groups are presently rare and expensive but their diagnosis is of increasing importance due to increasing likelihood in modern medicine of multiple blood transfusions and the hazard thus raised of a recipient having, unknowingly, been previously sensitized.

The demonstrations contained in this invention show that the synthesized determinants can be used for the preparation of highly effective monospecific immunoadsorbents. These immunoadsorbents promise to have important and wide utility for the removal of undesired antibodies from blood sera and for the isolation and purification of specific antibodies through absorption-desorption procedures. In this latter regard, the utility of incomplete determinants for the preparation of affinity chromatograms is of substantial significance since the use of complete determinants can lead to binding of the antibodies that is so strong that the desorption cannot be accomplished without extensive denaturation of the antibody and, thereby, loss of its specificity.

The above-mentioned benefits accruing as the result of the discoveries leading to this invention are demonstrated by Examples XII to XIX presented below. These examples were selected from a large list of similar investigations leading to this invention and were chosen so as to well establish the spirit and scope of the invention in terms of the utility of determinants and carrier molecules to prepare artificial antigens and of determinants and solid supports to prepare immunodsorbents.

The attachments of the determinants beginning with the ester grouping contained in the structure-types II, III, IV and V can be made following several procedures well known to this area of investigation. The most direct way is by straightforward aminolysis of the ester on the bridging arm using dry methanol as solvent,

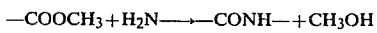

the amide grouping serving as the linkage between hapten and carrier or solid support.

A second method comprises first converting the ester to the free carboxylic acid followed by condensation of the acid with amino groups using suitable condensing agents such as dicyclohexyl and other carbodiimides or 1-ethoxycarbonyl-2-ethoxy-1,2-dihydroquinoline (EEDQ),

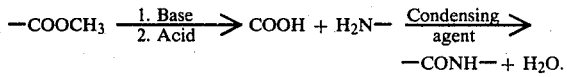

A third method (and that preferred) involves conversion of the ester to hydrazide followed by nitrous oxidation of the hydrazide to form the acyl azide which serves as acylating agent,

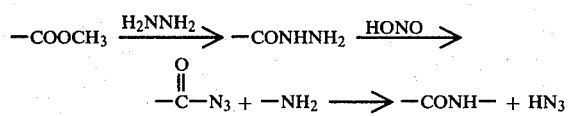

In these various ways artificial antigens are prepared by coupling the synthesized determinants to soluble carrier macromolecules such as the proteins bovine serum albumin (BSA) human serum albumin (HSA) and polylysine, to red blood cells, and to polysaccharides such as aminated dextran. Also, immunoadsorbents are prepared using solid supports such as aminated sepharose, aminated polystyrene, polyvinylamine, aminated polyvinylalcohol, aminated polyacrylamide, aminated glass, aminated calcined diatomaceous earth and aminated diatomaceous earth. These solids normally are employed as beads or latex particles but may be used on surfaces of tubes and plates depending on the use for the antigenic surface; that is, as an insoluble adsorbent for the extraction of antibodies, for the preparation of an affinity chromatographic column, for the detection of agglutination-type phenomena as for spot tests on surfaces, etc.

The artificial antigens reported in Examples XII to XVI were tested by administration to experimental animals; mainly rabbits and goats. For rabbits the immunization protocol was that described by Martineau[2] and for goats that of Marcus and Grollman[3]. The course of the immunization was followed by quantitative precipitin tests on samples of blood withdrawn at various times. The procedures used were all standard to the field of immunology[4].

EXAMPLE XII

The antigen ($\beta$-D-gal-O(CH$_2$)$_8$CONH)$_{24}$-BSA (12)

Compound 1 (1 g) was dissolved in a mixture of ethanol (5 ml) and 85% hydrazine hydrate (2 ml). After 24 h the solvent was evaporated and residual traces of hydrazine removed by co-evaporation with toluene to give 8-hydrazinocarbonyloctyl $\beta$-D-galactopyranoside as a white solid which was recrystallized from ethanol, mp 194°, $[\alpha]_D^{18}$ −2.16° (c 1.1, water), 92% yield.

The hydrazide (88 mg, 0.25 mmol) was dissolved in DMF (3 ml) and the solution cooled to −25°. A 3.3 N solution of hydrogen chloride in dioxane (0.33 ml) was added and then tert-butyl nitrite (36 mg, 0.35 mmol) in DMF (0.1 ml). After 30 min, sulfamic acid (20 mg) was added and the stirring was continued for 15 minutes. The acyl azide solution was then added directly to a 0° solution of bovine serum albumin (BSA) (300 mg) dissolved in an aqueous solution 0.08 M in Na$_2$B$_4$O$_4$ and 0.35 M in KHCO$_3$. The pH of the solution remained between 9.05 and 9.30 during the course of the addition. After 16 h the solution was dialyzed against water and freeze dried to provide antigen 12 (310 mg) as a white powder. Incorporation of galactose was determined by the phenol sulfuric acid method and calculated to be 24 moles galactose per mole of BSA.

A group of six San Juan rabbits were immunized with antigen 12 incorporated into Freund's complete adjuvant (FCA). The amount of conjugate administered and the immunization schedule followed the protocol described by Martineau et al.[2] Antibody levels upon completion of the schedule ranged from 178 to 396 $\mu$g per 50 $\mu$l of sera with the average being 277 $\mu$g per 50 $\mu$l sera.

That the antibodies raised to this conjugate are directed mainly toward the $\beta$-galactopyranoside portion of the antigen was demonstrated by measuring the maximum amount of antibody precipitated by three antigens 12, ($\alpha$-D-gal-O(CH$_2$)$_8$CONH)$_{17}$-BSA, and BSA. Typically for 50 $\mu$l of crude sera the results were as follows: antigen 12, 396 $\mu$g; ($\alpha$-D-gal-O(CH$_2$)$_8$CONH)$_{17}$-BSA, 87 $\mu$g; and BSA, 87 $\mu$g. Thus, it is possible to conclude that the greatest portion of the antibody population recognizes specifically the $\beta$-D-gal portion of the hapten. This conclusion is reinforced by inhibition experiments which show that while methyl $\beta$-D-galactopyranoside gives 50% inhibition of precipitation [using ($\beta$-D-gal-O(CH$_2$)$_8$CONH)$_{23}$-HSA as the precipitating antigen] at a concentration of 0.83 $\mu$M/ml, compounds having similar structures require much larger concentrations to be effective; i.e. galactose require 6.6 $\mu$M/ml; methyl $\alpha$-D-galactopyranoside require 33 $\mu$M/ml; lactose require 70 $\mu$M/ml and methyl $\beta$-D-glucopyranoside gives approximately no inhibition.

EXAMPLE XIII

The antigen ($\beta$-D-glcNAc-O(CH$_2$)$_8$CONH)$_{25}$-BSA (13)

This antigen was prepared from the hydrazide derivative of compound 2 using the acyl azide coupling method described in example XII. Sera obtained from rabbits immunized with 13 showed a high specificity for antigens containing the $\beta$-D-glcNAc hapten. Proof of the hapten specific nature of the response comes from hapten specific inhibition of precipitation between 13 and antisera raised to 13. Typically, methyl $\beta$-D-glcNAc gave inhibition of precipitation in the range of 60–80%, while methyl $\beta$-D-galNAc and methyl $\beta$-D-glc gave virtually no inhibition at the concentration that methyl $\beta$-D-glcNAc was effective.

EXAMPLE XIV

The Lewis-a antigens

Compound 8 (1 g) was dissolved in 85% hydrazine hydrate (4 ml) and allowed to stand for 4 h at ambient temperature. The reaction mixture was diluted with 95% ethanol (20 ml) and the solvents evaporated. The residue was dissolved in 10 ml water and dialyzed against 5 changes of water in an ultrafiltration cell. Lyophilization of the water gave 8-hydrazinocarbonyloctyl 2-acetamido-2-deoxy-4-O-($\alpha$-L-fucopyranosyl)-3-O-($\beta$-D-galactopyranosyl)-$\beta$-D-glucopyranoside (14) in quantitative yield as an amorphous solid, $[\alpha]_D$ −72.8° (c 1.0, water). This compound and the 5-hydrazinocarbonylpentyl analog were used to prepare the following Lewis-a antigens [Le$^a$-O(CH$_2$)$_8$CONH]$_n$-BSA where n can have any of the following values 11, 22, 30, or 45; [Le$^a$-O(CH$_2$)$_8$CONH]$_{28}$-HSA; [Le$^a$-O(CH$_2$)$_8$CONH]$_{15}$-polylysine; [Le$^a$-O(CH$_2$)$_8$CONH(CH$_2$)$_2$NH]$_{10}$-dextran; [Le$^a$-O(CH$_2$)$_5$CONH]$_n$-BSA where n was 10 or 30;

[Le$^a$-O(CH$_2$)$_5$CONH]$_{25}$-HSA by the acyl azide method (cf example XII). The abbreviation Le$^a$ as used above stands for the Lewis-a trisaccharide determinant:

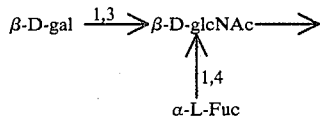

Goat antiserum prepared against the natural Lewis-a blood group substance was found to form a precipitate with the above Le$^a$ antigens.

Using the above Le$^a$ antigens it was possible to examine the effect of factors such as length of the bridging arm and level of hapten incorporation on the immune response to raise antisera specific for the Lewis-a blood group. Antibody levels of sera raised in rabbits to the Le$^a$-BSA antigens possessing C$_6$ and C$_9$ aglyconic "bridging arms" suggest very little variation due to the 3 methylene difference between the two antigens, especially at incorporations of 30 haptens/mole of BSA. At 11 haptens/mole of BSA the Le$^a$-BSA antigen with a C$_9$ bridging arm gave titers averaging about 50% higher than the C$_6$ analog. The level of hapten incorporation also affected antibody production. For rabbits it appeared that an incorporation of about 22 moles of hapten/mole of BSA gave an optimum response in terms of antibody level and specificity. At lower levels of hapten incorporation (~11 moles/mole BSA) increasing amounts of antibody in the sera had a specificity for the carrier, while at higher levels of incorporation (~30 moles/mole BSA) antibody titers were generally lower.

The specificity of the antisera was demonstrated by immunodiffusion reactions. Rabbit antisera raised to Le$^a$-BSA antigens showed a strong line of precipitation with all the artificial Le$^a$ antigens and the natural Lewis-a blood group substance and a very weak line of precipitation was shown with BSA. No line of precipitation was seen with HSA, polylysine or dextran.

To further explore the extent of cross reactions between antibodies raised to the artificial Le$^a$ antigens and human Lewis-a blood group substance and to obtain larger amounts of antisera, a goat was immunized with [Le$^a$-O(CH$_2$)$_8$CONH]$_{30}$-BSA. The antisera obtained showed the expected cross-reaction with human Lewis-a blood group substance and after appropriate treatment effectively agglutinated human blood group Lewis-(a+b−) red cells and did not agglutinate Lewis (a−) red cells. The goat preimmune sera treated in the same manner did not agglutinate Lewis-a red cells.

EXAMPLE XV

The H(O) antigens

Artificial antigens bearing the H(O) type I determinant

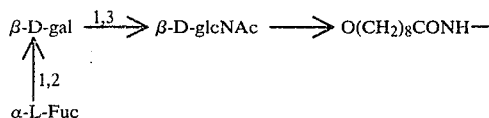

were prepared from compound 9 by the methods described in example XIV. Five rabbits underwent immunization with the antigen [H(O)]$_{22}$-BSA. On immunodiffusion, the antisera reacted weakly with BSA but strongly with the artificial antigens and human H substance.

Goat antisera were prepared against the natural blood substance H. The artificial antigen was found to form a precipitate with the resulting antiserum when tested by immunodiffusion. Thus, it is apparent antiserum specific for the terminal trisaccharide unit of the type I H-determinant was successfully raised.

EXAMPLE XVI

The B antigens

Artificial antigens bearing the B determinant

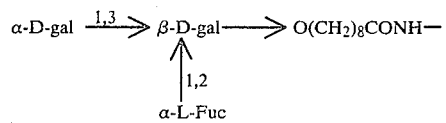

were prepared from compound 10 by the methods described in Example XIV. It was found that the artificial B antigens strongly inhibited agglutination of B cells by human anti-B sera. Goat antisera prepared against the natural blood group B substance was found to form a precipitate with the artificial B antigens.

EXAMPLE XVII

Lewis-a immunoadsorbents

Porous glass beads (100–200 mesh, nominal exclusion limit 1000 Å) were "animated" using 3-aminopropyltriethoxysilane under standard conditions.[5] The amine content was 69 μM per gram as estimated by the procedure of Esko et al.[6]

The Lewis-a hapten precursor (10 mg, 14.3 μM) (8-hydrazinocarbonyloctyl 2-acetamido-2-deoxy-4-O-(α-L-fucopyranosyl)-3-O-(β-D-galactopyranosyl)-β-D-glucopyranoside) was converted to acyl azide (cf example XIV) for coupling to 5 g of the "animated" glass beads. The excess amino groups were then acetylated by treatment for 20 min at room temperature with 5% acetic anhydride in aqueous saturated sodium bicarbonate. The beads were then washed with water and air dried to provide immunoadsorbent GB-Le$^a$-1.

When GB-Le$^a$-1 (50 mg) was added to 250 μl of anti-Le$^a$-BSA rabbit serum, the adsorption of Le$^a$ antibody was complete within 30 min as estimated by immunodiffusion. Using 25 mg of the adsorbent, the antibody removal took near 3 hours. With 10 mg, a small amount of residual antibody could be detected after 5 hours.

The above antiserum had been raised against the artificial Lewis-a antigen [Le$^a$-O(CH$_2$)$_8$CONH]$_{30}$-BSA. The maximum precipitation against [Le$^a$-O(CH$_2$)$_8$CONH]$_{28}$-HSA as test antigen was 277 μg of antibody per 50 μl of antiserum.

The immunoadsorbent GB-Le$^a$-1 was also tested against an anti-Lewis-a serum raised in a goat using natural Lewis-a blood group substance. The presence of 60 mg of the a sorbant in 250 μl of this antiserum caused disappearance of the antibody in the supernatent serum in less than 45 min.

No discernible antibody adsorption occurred when N-acetylated "aminated" glass beads were used as control.

EXAMPLE XVIII

H(O) immunoadsorbents

An immunoadsorbent specific for anti-H antibodies was prepared by coupling compound 9 to glass beads (cf example XVII). This immunoadsorbent was able to adsorb from sera antibodies raised to both artificial H antigens and natural H substance.

EXAMPLE XIX

B immunoadsorbents

An immunoadsorbent specific for anti-B antibodies was prepared by coupling compound 10 to glass beads (cf example XVII). This immunoadsorbent (GB-B-1) was able to adsorb from sera antibodies raised to both artificial B antigens and natural B substance. This immunoadsorbent also removed anti-B antibodies from typing sera.

Using a panel of fresh B cells suspended in saline the test serum gave positive agglutination to a dilution of 1 to 32. Under the same conditions H(O) cells showed no agglutination. The immunoadsorbent, GB-B-1, (50 mg) was added to 250 μl of sera after 45 min 150 μl of sera was withdrawn and tested against B cells suspended in saline. There was no agglutination of the cells indicating the anti-B antibodies had been removed.

No discernible antibody adsorption occurred when N-acetylated "aminated" glass beads were used as control.

To prepare a B immunoadsorbent having a polyacrylic support, a resin containing carboxylic acid groups on an acrylic polymer lattice (10 ml) was treated with a mixture of ethylene diamine (21 g), 1-cyclohexyl-3-(2-morpholino-ethyl)carbodiimide metho-p-toluenesulfonate (15 g) in 100 ml of water for 24 h (the pH of the solution was maintained at 5 by the addition of concentrated hydrochloric acid). The resin was filtered off, washed with water and air dried.

N-Ethoxycarbonyl-2-ethoxy-1,2-dihydroquinoline mediated condensation of 8-hydroxycarbonyloctyl 2-O-(α-L-fucopyranosyl)-3-O-α-D-galactopyranosyl-β-D-galactopyranoside (10 μM/ml resin) (prepared from 10 by hydrolysis of the ester) with the "aminated" resin, followed by N-acetylation of the unreacted amino groups gave the desired B immunoadsorbent. This immunoadsorbent also selectively removed anti-B antibodies from B antisera.

A B immunoadsorbent having an agarose matrix was also prepared by condensing 10 with "aminated" agarose.

The synthesis of the B, H(O) type I and Lewis-a and -b antigenic determinants has been described above. The following additional Examples detail the synthesis of determinant of other blood group antigens and provide additional examples of the utility of products derived from these compounds.

In the first example below, the preparation of the blood group B related antigenic determinant 8-methoxycarbonyloctyl 3-O-α-D-galactopyranosyl-β-D-galactopyranoside is described. This compound can be considered as an "incomplete" B antigenic determinant in that it lacks the α-L-fucopyranosyl moiety at the 2-position of the β-D-galactopyranosyl group. It can be of considerable advantage to be able to prepare such "incomplete" determinants as, for example, it permits the fractionation of antibodies specific for a particular determinant into subset populations having affinities for different portions of the whole determinant.

EXAMPLE XX

The antigenic determinant 8-methoxycarbonyloctyl 3-O-α-D-galactopyranosyl-β-D-galactopyranoside To a cold ($-79°$ C.) solution of crude 8-methoxycarbonyloctyl-4,6-O-benzylidene-β-D-galactopyranoside[13] (123 g, 0.28 mole) in dry, distilled, dichloromethane (2.8 l) and pyridine (27.3 ml, 0.34 mole), distilled chloroacetyl chloride (23.3 ml, 0.34 mole) in dry dichloromethane (100 ml) was added dropwise over a period of 2 h. The temperature was allowed to raise to $-10°$ C. and the solution was poured into vigorously stirred water (5 l). The organic phase was separated and washed with water (2×1 l). The combined organic phases were dried over sodium sulfate, filtered and evaporated in vacuo to give 143.6 g (99%) of a pale yellow syrup. The purity was estimated by tlc (EtOAC: 1,1: Skellysolve B), $^1$H nmr and $^{13}$C nmr to be at least 85–90%.

The above compound (140 g, 0.27 mole) in dry dichloromethane (1.4 l) containing dry, distilled, pyridine (45 ml, 0.55 mole) and a few crystals of 4-N,N-dimethylaminopyridine, distilled benzoyl bromide (66 ml, 0.55 mole) in dry dichloromethane (45 ml) was added dropwise. The reaction was monitored by tlc (EtOAC: 6,4: Skellysolve B, eluted twice) and took approximately 4 h. When no starting material was detectable by tlc, the solution was poured into vigorously stirred cold water (2 l), the organic phase was separated and then washed twice with water (1000 ml). After drying over sodium sulfate, the organic phase was evaporated to give 218 g of a yellow syrup. The purity of this product was estimated by $^1$H nmr, $^{13}$C nmr and tlc to be 80–90%.

To a cold suspension ($-30°$ C.) of crude 8-methoxycarbonyloctyl-2-O-benzoyl-4,6-O-benzylidene-3-O-chloroacetyl-β-D-galactopyranoside (215 g) in dry methanol (2 l), saturated (at $-5°$ C.) methanolic ammonia (180 ml) was added. The suspension became immediately a clear solution and the reaction was monitored by tlc (EtOAC: 1,1: Skellysolve B). When no starting material was detectable, the ammonia was evaporated by suction (water pump) while the temperature was allowed to raise to 0° C. When no ammonia was left, the methanol was evaporated in vacuo and the resulting solid was dissolved in dichloromethane (1.5 l). The solution was washed successively with water (2×300 ml), saturated sodium bicarbonate (300 ml) and water again (300 ml). The combined organic phases were dried over sodium sulfate before being evaporated to a yellow syrup (165 g). The tlc indicated that the major product was the desired compound. The syrup was purified by column chromatography on silica gel (3.3 kg) using a stepwise-gradient elution. Weight of white solid 95 g (77% from 8-methoxycarbonyloctyl-4,6-O-benzylidene-β-D-galactopyranoside). A sample was recrystallized from 98% ethanol to give an analytical sample; mp 119°-120° C., $[\alpha]_D^{24} +7.1°$ (c 1, CHCl$_3$).

Anal. Calcd. for $C_{30}H_{38}O_9$: C, 66.4; H, 7.06,. Found: C, 66.21; H, 7.09.

The compound 2-acetamido-3-O-acetyl-6-O-benzoyl-2-deoxy-β-D-glucopyranoside was previously described (13). Condensation of this compound with 3,4,6-tri-O-acetyl-2-O-(2,3,4-tri-O-benzyl-α-L-fucopyranosyl)-α-D-galactopyranosyl bromide under Koenigs-Knorr type conditions provided 8-methoxycarbonyloctyl 2-acetamido-3-O-acetyl-6-O-benzoyl-4-O-[3,4,6-tri-O-acetyl-2-O-(2,3,4-tri-O-benzyl-α-L-fucopyranosyl)-α-D-galactopyranosyl]-2-deoxy-β-D-glucopyranoside. Removal of the blocking groups afforded α-L-fuc(1→2)β-D-gal(1→4)β-D-glcNAc-O(CH$_2$)$_8$COOCH$_3$, the trisaccharide determinant for the H (Type II) human blood determinant. It is now clear that similar synthetic strategies can lead to the A and B (Type II) tetrasaccharide determinants in accordance with the present invention. Through such synthetic strategies, the A and B (Type I) tetrasaccharide determinants conforming to the generic structure have been prepared. The procedure was to prepare 8-methoxycarbonyloctyl 2-acetamido-3-O-4,6-O-benzylidene-2-deoxy-β-D-glucopyranoside, then to preferentially benzoylate the 3'-position as described in earlier Examples and continuing from this precursor in essentially the same manner as was used to prepare the B-trisaccharide hapten. For the preparation of the A-tetrasaccharide hapten, 3,4,6-tri-O-acetyl-2-azido-2-deoxy-β-D-galactopyranosyl chloride was condensed with the selectively blocked α-L-fuc(1→2)-β-D-gal(1→3)-β-D-glcNAc glycoside. Reduction and N-acetylation of the azido group and removal of the other hydroxyl blocking groups gave the desired A determinant.

Using now well established synthetic methodologies, the following oligosaccharide 8-methoxycarbonyloctyl-glycosides were also synthesized. The structures, β-D-gal(1→4)-β-D-glcNAc(1→6)-β-D-gal and β-D-gal(1→4)-β-D-glcNAc(1→3)-β-D-gal, provided haptens with activities related to the I and i human blood groups (15,16) (cF Example XIII) and the structures β-D-galNAc(1→3) α-D-gal(1→4) β-D-gal(1→4) β-D-glc; α-D-gal(1→4) β-D-gal(1→4) β-D-glcNAc(1→3) β-D-gal; and α-D-gal(1→4) β-D-gal(1→4) β-D-glc gave respectively P, P$_1$ and P$^k$ (17) active haptens.

The blood group antigenic determinants obtained through the general procedures disclosed herein can be used to prepare many products useful to medical science. Some particular applications will now be discussed to illustrate the wide range of utility of these synthetic oligosaccharide determinants.

As various factors have combined to make human antisera to minor blood groups increasingly difficult to obtain and at the same time demand for the antisera has increased, it has become necessary to turn to animals for the production of these rare antisera. The artificial antigens bearing determinants of defined structure and the monospecific adsorbents obtainable through the procedures embodied herein provide the materials necessary for a greatly simplified process for the production of various antisera. In Example XXI, the preparation of a Lewis-a red cell agglutinating antisera is described.

EXAMPLE XXI

Preparation of Anti-Lewis-a

A goat was immunized[3] with [Le$^a$-O(CH$_2$)$_8$CONH]$_{30}$-BSA and after about 6 weeks 200 ml of blood was collected. After separation of the serum an aliquot (50 ml) was applied (40 ml/h) to a 20 g immunoadsorbent column prepared by coupling the same Lewis-a hapten to silylaminated calcined diatomaceous earth (100/120 mesh) using the procedures previously described. After passage of the serum the column was washed with 200 ml of phosphate buffered saline (PBS) and the antibodies bound to the column were desorbed with 2% ammonium hydroxide in 0.15 M saline. The ultraviolet absorbing (280 nm) eluate was collected, neutralized (pH 7.2) with a saturated solution of KH$_2$PO$_4$, dialysed against PBS and concentrated to a final volumn of 25 ml.

The protein concentration of the antibody solution was 5.4 mg/ml as determined by the UV absorption at 280 nm using goat IgG as a standard. Examination of the solution by electrophoresis (barbital buffer, pH 8.6, cellulose acetate membrane) showed only a single band with a mobility similar to that of goat IgG.

When diluted in a ratio of 1 to 4 with 1% bovine serum albumin in PPS the resulting solution was found to selectively agglutinate human Lewis-a red cells (titre ⅛ to 1/16). In an examination of over two hundred random samples, all Lewis-a positive red cells were detected and there were no false postive agglutinations.

In addition to the isolation of antibodies from immune sera, it is also possible to recover antigens present only in low titre and concentrate them so as to afford a high titre antibody solution. This procedure is illustrated in Example XXII where anti-B and A are isolated from random pooled human sera.

EXAMPLE XXII

Preparation of high titre Anti-B from human sera

To a column (175 g) of B immunoadsorbent (prepared by coupling α-L-fuc(1→2)[α-D-gal(1→3)]β-D-gal O(CH$_2$)$_8$CON$_3$[13] to silylaminated calcined diatomaceous earth as in Example XXI was applied pooled human A sera (2.5 l, saline titre ~⅛) at a flow rate of 200 ml/h. Following application of the serum, the column was washed with PBS (1.2 l) and the antibodies desorbed as in Example XXI. The dialysed antibody solution was concentrated to a volume of about 70 ml and 5 ml of human A serum was added as a stabilizer.

This procedure afforded an antisera with a saline anti-B titre of 1/5000. No other antibody activity was detectable by red cell panels. Dilution of this antisera with 1% bovine serum albumin in PBS (1% BSA/PBS) in the ratio of 1:4 (antisera: 1% BSA/PBS) gave an antisera with an anti-B titre of 1/512 which met or exceeded approved government standards for Anti-B blood grouping sera.

To investigate the effect of "completeness" of the antigenic determinant for the removal of naturally-occurring anti-B two immunoadsorbents having different B determinant structures were prepared and their efficiency in adsorbing anti-B compared. The first adsorbent was the B trisaccharide hapten coupled materials described above, the second contained the α-D-gal(1→3)βgal disaccharide described in Example XX coupled to the same solid support as described above.

To identical 5 g columns of each immunoadsorbent were applied 50 ml aliquots of human A serum. After about 25 ml of sera had passed through the columns a 1 ml aliquot of the eluted sera was collected and examined for the presence of B agglutinins. In the majority of cases the performance of the adsorbents were comparable, with all anti-B agglutinins being removed; however, it was observed that for some sera the efficiency of the disaccharide adsorbent was inferior to that of trisaccharide in removing anti-B. Comparable columns of unhaptenated solid support had no effect on the anti-B titre.

Preparation of high titre Anti-A from human sera

Using the same general procedure given for the preparation of anti-B but using the immunoadsorbent prepared from α-L-fuc(1→2)[α-D-galNAc(1→3)]β-D-gal O(CH$_2$)$_8$CO$_2$CH$_3$ anti-A antibodies were isolated from 2.4 l of pooled human B serum. From this sera pool 125 ml of anti-A with a saline titre of 1/512 was obtained.

Frequently the objective in serological investigations is not the removal of an antibody, but the identification of the specificities of antibodies present in serum or other biological fluids as the presence of certain "atypical" antibodies can be clinically important in many situations. For example, in North America, the serum of pregnant and recently delivered women is routinely examined for the presence of irregular antibodies which might be indicative of an incompatible pregnancy or other pathological condition.

When the presence of an irregular antibody is detected, the specificity of the antibody or antibodies is determined by means of a cell panel. That is, the agglutination pattern of a collection of group O cells bearing known antigens is examined in the hope that by a process of elimination the nature of the antibodies present may be determined. In cases where more than one antibody is present, deducing the specificities of the antibodies present is much more complicated. The ability of immunoadsorbents bearing defined determinants to selectively remove various antibody populations simplifies and makes more certain this identification process as is illustrated in Example XXIII.

EXAMPLE XXIII

Adsorption of atypical anti-Lewis-a and anti-I antibodies from human serum

The patient L. H. was admitted to hospital following a spontaneous miscarriage. Routine blood tests showed the presence of atypical antibodies and agglutination tests with a cell panel showed reaction with 9 out of 10 cell types at ambient temperature and reaction with 3 out of 10 at 37°. Because of the widespread agglutination, no definite pattern was discernible; however, as some of the Lewis-a positive cell types were hemolysed by the patient's serum, one of the antibodies present was tentatively identified as anti-Lewis-a[18]. To confirm this identification a 1 ml aliquot of the patient's serum was tumbled with Lewis-a adsorbent (cf Example XXI) for 20 min at room temperature and after removal of the adsorbent by centrifugation the agglutination pattern was again examined. There was now no agglutination of the cell panel at 37°, however, the ambient temperature agglutination was still present. Similar treatment of another aliquot with a Lewis-b adsorbent under the same conditions did not change the agglutination pattern. On the basis of these results one of the antibodies present was definitely identified as an anti-Lewis-a.

Because of the generality of the room temperature agglutination even after the removal of the anti-Lewis-a, the presence of atypical warm reactive anti-I was suspected. Adsorption of the Lewis-a adsorbed serum at 4° with a calcined diatomaceous earth adsorbent bearing the hapten β-D-gal(1→4)β-D-glcNAc(1→6)β-D-gal resulted in a marked decrease in the agglutination strength of the serum indicating that the remainder of the antibodies were likely warm reactive anti-I. Additional confirmation for this hypothesis was obtained when it was found that the Lewis-a adsorbed serum did not agglutinate cord cells which lack the I antigen.

As was pointed out earlier, some of the so-called blood group antigenic determinants can be found in other tissues and biological fluids such as serum and saliva. The ability to detect these antigens, other than on the red cell, can be important in instances when the red cells are not available such as in forensic examinations or in organ transplant when the antigens on the tissue may not be the same as on the red cell. In all these cases, since the antigens are typically present only in very small amounts and in combination with large quantities of similar materials, very sensitive and specific methods must be used. At present the best methods for detection of particular chemical structures under these conditions involves the use of antibody molecules labelled in some way so that their interaction with the tissue or fluid in question can be monitored. Much ingenuity has been expended in developing these detection methods, however, in every case the ultimate success depends on obtaining highly purified monospecific antibodies. As has been already shown, the techniques disclosed in this invention lend themselves very well to the production and isolation of monospecific antibodies to carbohydrate blood group antigens; demonstrations of the utility of these antibodies for the detection of antigens in tissue sections (Example XXIV) and serum (Example XXV) will now be detailed.

EXAMPLE XXIV

Detection of Lewis-a and b antigens in the human kidney by immunofluorescence

Human kidney tissue samples were obtained by needle biopsy and conventionally fixed and imbedded in paraffin. Tissues were sectioned to 4 microns, placed on a slide and deparaffinized using organic solvents. To detect the Lewis antigens a sample was incubated for 1 h with affinity purified rabbit anti-Lewis-a or b raised to the corresponding artificial antigen (antibody concentration 0.5 mg/ml in 1% BSA/PBS). The samples were then washed with PBS and treated with fluorescein conjugated goat anti-rabbit for 1 h and again washed with PBS. Fluorescence was detected by observation with a fluorescence microscope.

Lewis antigens corresponding to the Lewis red cell type were found to be localized only in the collecting tubules of the kidney. In all cases, the Lewis type found in the kidney corresponded to that on the red cell. Specimens from Lewis a- b- subjects showed no Lewis-a or -b antigens in their kidneys.

Using these affinity purified anti-Lewis antibodies, background staining was essentially eliminated. The increased sensitivity and specificity of these reagents is testified to by the fact that previous workers[19] had been unable to detect Lewis antigens in the human kidney.

EXAMPLE XXV

The detection of Lewis-a antigens in serum

Conical bottomed plastic tubes (10×25 mm) were coated with antibody by adding to each tube 50 μl of an aqueous solution (∼10 μg/ml) of goat anti-Lewis-a (cf Example XXI) and incubating the tubes with the coating solution for 5 min. The solution was then removed by aspiration and the tubes washed three times with 0.5 ml water. The serum samples (10 μl) were diluted to 60 μl with 1% BSA/PBS and added to the coated tubes and incubated for 1 h. The sample was then removed by aspiration and then ~1 ng of $^{125}$I-labelled BSA-Lewis-a antigen (~50,000 cpm) in 50 μl 1% BSA/PBS was added. After a further 1 h the tubes were washed with water (3×1 ml) and the tube bound $^{125}$I BSA-Lewis-a measured. Results for a typical run are given in Table 1.

As can be seen, the Lewis-a samples (3, 7 and 9) are easily detected by their marked inhibition of binding of the $^{125}$I-labelled BSA-Le$^a$ artificial antigen.

TABLE I
LEWIS-a RADIOIMMUNOASSAY OF HUMAN SERUM

| Sample | Serum added | CPM bound | Lewis-a | RBC test |
|---|---|---|---|---|
| Blank | — | 11600 | — | — |
| Le$^a$ control | 10 μl Le$^{a+}$ | 2313 | + | A Le$^{a+\ b-}$ |
| Le$^b$ control | 10 μl Le$^{b+}$ | 11453 | — | A Le$^{a-\ b+}$ |
| 1 | 10 μl | 10766 | — | O Le$^{a-\ b+}$ |
| 2 | 10 μl | 11453 | — | B Le$^{a-\ b+}$ |
| 3 | 10 μl | 1529 | + | A Le$^{a+\ b-}$ |
| 4 | 10 μl | 11569 | — | A Le$^{a-\ b+}$ |
| 5 | 10 μl | 10103 | — | O Le$^{a-\ b+}$ |
| 6 | 10 μl | 11012 | — | A Le$^{a-\ b-}$ |
| 7 | 10 μl | 1208 | + | A Le$^{a+\ b-}$ |
| 8 | 10 μl | 10469 | — | A Le$^{a-\ b+}$ |
| 9 | 10 μl | 1860 | + | O Le$^{a+\ b-}$ |
| 10 | 10 μl | 10711 | — | A Le$^{a-\ b+}$ |

REFERENCES

1. R. U. Lemieux, D. R. Bundle, and D. A. Baker, J. Amer. Chem. Soc., 97, 4076 (1975).
2. R. S. Martineau, P. Z. Allen, I. J. Goldstein, R. N. Iyer, Immunochemistry, 8, 705 (1971).
3. D. M. Marcus and A. P. Grollman, J. Immunol., 97, 867 (1966).
4. E. A. Kabat and M. M. Mayer, "Experimental Immunochemistry", 2nd ed., Oliver and Boyd, London, 1967.
5. H. H. Westal and A. M. Filbert, "Methods of Enzymology", 34 (b), 64 (1974).
6. K. Esko, S. Karlson, and J. Porath, Acta Chem. Scand., 22, 3342 (1968).
7. O. Th. Schmidt, Methods in Carbohydrate Chemistry, I, 349 (1962).
8. P. Z. Allen, Methods in Carbohydrate Chemistry, I, 372 (1962).
9. E. A. Talley, Methods in Carbohydrate Chemistry, II, 337 (1963).
10. H. M. Flowers, Methods in Carbohydrate Chemistry, VI, 474 (1972).
11. N. K. Kochetkov and A. F. Bochkov, Methods in Carbohydrate Chemistry, VI, 480 (1972).
12. S. E. Zurabayan, T. S. Antonenko and Ya. Khorlin, Carbohydrate Research, 15, 21 (1970).
13. R. U. Lemieux, D. R. Bundle and D. A. Baker, U.S. Patent Application Ser. No. 698,548, Artificial Oligosaccharide Antigenic Determinants, U.S. Pat. No. 4,137,401, dated Jan. 30, 1979.
14. V. P. Rege, T. J. Painter, W. M. Watkins and W. T. J. Morgan, Nature 203, 360 (1964).
15. E. A. Kabat, J. Liao and R. U. Lemieux, Abstracts (II) XVII Congress Int. Soc. Hem and XV Congress Int. Soc. Blood Trans., p. 641, (1978).
16. H. Niemann, K. Watanabe, S. Hokomori, R. A. Childs, and T. Feizi, Biochem. Biophys. Res. Comm. 81, 1286 (1978).
17. M. Naiki and D. M. Marcus, Biochem. Biophys. Res. Comm. 60, 1105 (1974). ibid Biochem. 14, 4837 (1975).
18. P. L. Mollison, Blood Transfusion in Clinical Medicine, 5th ed., Blackwell Scientific Publications, Oxford 1972, p. 254.
19. A. E. Szulman and D. M. Marcus, Laboratory Investigations 28, 565 (1973).

We claim:

1. Lower oligosaccharide compounds active as blood group determinants having aldoses O-α or O-β-glycosidically linked to form di-, tri-, or tetra-saccharides, and having a bridging arm O-β-glycosidically linked to one of the aldose moieties, the bridging arm having the structure:

O—R—COR'' where R is a saturated aliphatic hydrocarbon moiety having from 3 to 17 carbon atoms and R'' is —H, —OH, —NH$_2$, —NHNH$_2$, —N$_3$ or lower alkoxy; the aldoses being selected from the group consisting of glucose, galactose, mannose, fucose, glucosamine, and acetamidodeoxyglucose, said aldoses and their sequence and linkage configurations being chosen to give active blood group determinants.

2. The lower oligosaccharides of claim 1 wherein R is the —C$_n$H$_{2n}$— grouping and n=8–10.

3. The lower oligosaccharide of claim 1 wherein the following sugars form the Lewis-a trisaccharide blood group determinant:
β-D-gal attached to the 3-position of β-D-glcNAc and α-L-fuc attached to the 4-position of β-D-glcNAc.

4. The lower oligosaccharide of claim 1 wherein the following sugars form the Lewis-b tetrasaccharide blood group determinant:
β-D-gal attached to the 3-position of β-D-glcNAc and α-L-fuc attached to the 2-position of β-D-gal and another α-L-fuc attached to the 4-position of β-D-glcNAc.

5. The lower oligosaccharide of claim 1 wherein the following sugars form the A tetrasaccharide (Type I) blood group determinant:
α-D-galNAc attached to the 3-position of β-D-gal and α-L-fuc attached to the 2-position of β-D-gal and the β-D-gal attached to the 3-position of β-D-glcNAc.

6. The lower oligosaccharide of claim 1 wherein the following sugars form the A trisaccharide blood group determinant:
α-D-galNAc attached to the 3-position of β-D-gal and α-L-fuc attached to the 2-position of β-D-gal.

7. The lower oligosaccharide of claim 1 wherein the following sugars form the A disaccharide blood group determinant:
α-D-galNAc attached to the 3-position of β-D-gal.

8. The lower oligosaccharide of claim 1 wherein the following sugars form the B tetrasaccharide (Type I) blood group determinant:
α-D-gal attached to the 3-position of β-D-gal and α-L-fuc attached to the 2-position of β-D-gal and the β-D-gal attached to the 3-position of β-D-glcNAc.

9. The lower oligosaccharide of claim 1 wherein the following sugars form the B trisaccharide blood group determinant:
α-L-fuc attached to the 2-position of β-D-gal and α-D-galactopyranose (α-D-gal) attached to the 3-position of β-D-gal.

10. The lower oligosaccharide of claim 1 wherein the following sugars form the B disaccharide antigenic determinant:

α-D-gal attached to the 3-position of β-D-gal.

11. The lower oligosaccharide of claim 1 wherein the following sugars form the H (Type I) blood group determinant:

α-L-fuc attached to the 2-position of β-D-gal which is attached to the 3-position of β-D-glcNAc.

12. The lower oligosaccharide of claim 1 wherein the following sugars form the H (Type II) determinant:

α-L-fuc attached to the 2-position of β-D-gal which is attached to the 4-position of β-D-glcNAc.

13. The lower oligosaccharide of claim 1 wherein the following sugars form the I related blood group determinant:

β-D-gal linked to the 4-position of β-D-glcNAc which is linked to the 6-position of β-D-gal.

14. The lower oligosaccharide of claim 1 wherein the following sugars form the i related blood group determinant:

β-D-gal linked to the 4-position of β-D-glcNAc which is linked to the 3-position of β-D-gal.

15. The lower oligosaccharide of claim 1 wherein the following sugars form the $P_1$ determinant:

α-D-gal attached to the 4-position of β-D-gal which is attached to the 4-position of β-D-glcNAc which is attached to the 3-position of β-D-gal.

16. The lower oligosaccharide of claim 1 wherein the following sugars form the P blood group determinant:

β-D-galNAc attached to the 3-position of α-D-gal which is attached to the 4-position of β-D-gal which is attached to the 4-position of β-D-glc.

17. The lower oligosaccharide of claim 1 wherein the following sugars form the Pk blood group determinant:

α-D-gal attached to the 4-position of β-D-gal attached to the 4-position of β-D-glc.

18. The lower oligosaccharide of claim 1 attached to a solid immunoadsorbent-type support or soluble, antigen-forming carrier macromolecule.

19. The lower oligosaccharide of claim 18 in the form of an artificial antigen or immunoadsorbent wherein the carrier or support is selected from the group consisting of antigen-forming proteins, red blood cells, aminated polysaccharides of the type dextran, sepharose, and agarose, aminated glass, aminated polystyrene, polyvinylamine, aminated polyacrylamide or aminated polyvinyl alcohol, aminated calcined diatomaceous earth or aminated diatomaceous earth.

20. A process for preparing oligosaccharide plus bridging arm compounds active as blood group determinants comprising:

(1) reacting (a) an activated aldose selected from the group consisting of an aldose halide, 1,2-orthoacyl ester-aldose, or 1,2-oxazoline-aldose, the aldose occurring in blood group determinants, with (b) a monohydroxy carboxylic acid of the structure HO—R—COOR' where R is a saturated aliphatic hydrocarbon moiety having from 3 to 17 carbon atoms and R' is a protecting alkyl group, to form an O-β-glycoside of the structure:

$$\text{Aldose} \xrightarrow{\beta} O-R-COOR';$$

(2) linking O-glycosidically in either the α- or β-anomeric configuration a further said aldose to the initial aldose moiety to form a disaccharide; the aldose reactants and their sequence and linkage configurations being controlled to give an active blood group determinant having the bridging arm —R—CO—, and (3) recovering the resulting blood group determinant hapten.

21. The process of claim 20 including further linking O-glycosidically in either the α- or β-anomeric configuration a further chosen aldose to the disaccharide moiety to form a trisaccharide of structure $$\text{trisaccharide} \xrightarrow{\beta} O-R-COOR'.$$

22. The process of claim 21 including the subsequent step of O-glycosidically linking in either the α- or β-anomeric configuration, a further aldose to the trisaccharide moiety to form a tetrasaccharide of structure $$\text{tetrasaccharide} \xrightarrow{\beta} O-R-COOR'.$$

23. A process according to claim 20 wherein the lower oligosaccharide plus bridging arm compound is further attached to an insoluble immunoadsorbent-type support or to a soluble antigen-forming carrier macromolecule.

24. The process of claim 23 wherein the bridging arm is attached to a support or carrier via an amide linkage involving the ω-carbonyl group of the ω-alkoxycarbonylalkyl bridging arm.

25. The process of claim 24 wherein said amide linkage is formed by reacting the carbonyl group of the bridging arm with amino groups of the support or carrier, using a soluble condensing agent selected from the group consisting of carbodiimide or 1-ethoxycarbonyl-2-ethoxy-1,2-dihydroquinoline.

26. The process of claim 24 wherein an amide linkage is formed between the carbonyl group of the bridging arm on the β-glycosides with OR' converted to $N_3$, and said support or carrier.

* * * * *

Disclaimer

4,238,473.—*Raymond U. Lemieux*, Edmonton, *David R. Bundle*, Ottawa, and *Donald A. Baker*, Edmonton, Alberta, Canada. ARTIFICIAL OLIGOSACCHARIDE ANTIGENIC DETERMINANTS. Patent dated Dec. 9, 1980. Disclaimer filed Oct. 9, 1981, by the assignee, *Chembiomed Ltd.*

Hereby enters this disclaimer to claims 6 and 7 of said patent.

[*Official Gazette December 15, 1981.*]